(12) United States Patent
Andrews et al.

(10) Patent No.: US 6,699,863 B1
(45) Date of Patent: Mar. 2, 2004

(54) KINASE INHIBITORS FOR THE TREATMENT OF DISEASE

(75) Inventors: Steven W. Andrews, Longmont, CO (US); Jonathan J. Hebert, Carlsbad, CA (US)

(73) Assignee: Allergan, Inc., Irvine, CA (US)

( * ) Notice: Subject to any disclaimer, the term of this patent is extended or adjusted under 35 U.S.C. 154(b) by 80 days.

(21) Appl. No.: 10/307,097

(22) Filed: Nov. 27, 2002

(51) Int. Cl.$^7$ ............... A61K 31/4015; A61K 31/5377; C07D 209/14; C07D 413/14

(52) U.S. Cl. ............... 514/235.2; 514/254.09; 514/323; 514/414; 544/144; 544/373; 546/201; 548/468

(58) Field of Search ............... 514/235.2, 254.09, 514/323; 544/144, 373; 546/201; 548/468

(56) References Cited

U.S. PATENT DOCUMENTS

| | | |
|---|---|---|
| 4,966,849 A | 10/1990 | Vallee et al. |
| 5,217,999 A | 6/1993 | Levitzki et al. |
| 5,302,606 A | 4/1994 | Spada et al. |
| 5,330,992 A | 7/1994 | Eissenstat et al. |
| 5,792,783 A | 8/1998 | Tang et al. |
| 5,834,504 A | 11/1998 | Tang et al. |
| 5,883,113 A | 3/1999 | Tang et al. |
| 5,883,116 A | 3/1999 | Tang et al. |
| 5,886,020 A | 3/1999 | Tang et al. |
| 6,316,635 B1 | 11/2001 | Tang et al. |

FOREIGN PATENT DOCUMENTS

| | | |
|---|---|---|
| WO | WO 91/15495 | 10/1991 |
| WO | WO 92/20642 | 11/1992 |
| WO | WO 92/21660 | 12/1992 |
| WO | WO 94/03427 | 2/1994 |
| WO | WO 94/10202 | 5/1994 |
| WO | WO 94/14808 | 7/1994 |
| WO | WO 01/90103 | 11/2001 |

OTHER PUBLICATIONS

Plowman et al, "Receptor Tyrosine Kinases as Targets for Drug Intervention",1994, DN&P 7(6): 334–339.
Bolen, "Nonreceptor tyrosine protein kinases", 1993, Oncogen 8: 2025–2031.
Kendall et al, "Inhibition of vascular endothelial cell growth factor activity by an endogenously encoded soluble receptor", 1994, Proc. Natl'l Acad. Sci 90: 10705–10709.
Kim et al, "Inhibition of vascular endothelial growth factor–induced angiogenesis suppresses tumor growth in vivo", Nature 362, 841–844.
Jellinek et al, "Inhibition of Receptor Binding by High–Affinity RNA Ligands to Vascular Endothelial Growth Factor", Biochemistry 33: 10450–10456 (1994).
Takano et al, "Inhibition of Angiogenesis by a Novel Diaminoanthraquinone that Inhibits Protein Kinase C.", 1993, Mol. Bio. Cell 4: 2072, pp. 358A.

Kinsella et al, "Protein Kinase C Regulates Endothelial Cell Tube Formation on Basement Membrane Matrix, Matrigel", 1992, Experimental Cell Research, 199: 56–62.
Wright et al, "Inhibition of Angiogenesis In Vitro and In Ovo With an Inhibitor of Cellular Protein Kinases, MDL 27032", 1992, Journal of Cellular Phys. 152: 448–457.
Mariani et al, "Inhibition of angiogenesis by FCE 26806, a potent tyrosine kinase inhibitor",1994, Proc. Am. Assoc. Cancer Res. 35:2268; p. 381.
Castro et al , "Quantitative Image Analysis of Laser–induced Choroidal Neovascularization in Rat", Exp. Eye Res. 2000; 71:523–55.
Bundgaard et al, "Hydrolysis of N–(α–hydroxyalkyl)amide derivatives: implications for the design of N–acyloxyalkyl–type prodrugs", Int. J. of Pharmaceutics 22 (1984); 45–56.
Bundgaard et al, ?Prodrugs as drug delivery systems, 43. O–Acyloxymethyl salicylamide N–Mannich bases as double prodrug forms for amines, Int. J. of Pharmaceutics 29 (1986); 19–28.
Bundgaard et al, "A Novel Solution–Stable, Water–Soluble Prodrug Type for Drugs Containing a Hydroxyl or an NH–Acidic Group", J. Med. Chem. 32 (1989) 2503–2507.
Bundgaard et al,"Prodrugs as drug delivery systems. XIX. Bioreversible derivatization of aromatic amines by formation of N–Mannich bases with succinimide", Chem. Abstracts 95, 138493f.
Bundgaard et al,"Hydrolysis of N–Mannich bases and its consequences for the biological testing of such agents", Chem. Abstracts 95, 138592n, date not available.
Alminger et al, "(Pyridinylmethyl)sulfinylbenzimidazole derivatives as antiulcer agents, their preparation and formulations containing them", Chem. Abstracts 110, 57664p, date not available.
Buur et al, "Prodrugs of cimetidine with increased lipophilicity; N–acyloxymethyl and N–alkoxycarbonyl derivatives", Chem. Abstracts 115, 64029s, date not available.
Hansen et al, "Carbamate ester prodrugs of dopaminergic compounds: synthesis, stability, and bioconversion", Chem Abstracts 115, 189582y, date not available.
Bundgaard et al, "Phenyl carbamates of amino acids as prodrugs forms for protecting phenols against first–pass metabolism", Chem. Abstracts 117, 14347q, date not available.
Jensen et al, N–Substituted (aminomethyl)benzoate 21–esters of corticosteroids as water–soluble, solution–stable and biolabile prodrugs, Chem. Abstracts 117, 55790x, date not available.
Thomsen et al, "Evaluation of phenyl carbamates of ethyl diamines as cyclization–activated prodrug forms for protecting phenols against first–pass metabolism", Chem Abstracts 123, 17593b, date not available.

*Primary Examiner*—Deborah C. Lambkin
*Assistant Examiner*—Sonya Wright
(74) *Attorney, Agent, or Firm*—Robert J. Baran; Martin A. Voet; Carlos A. Fisher

(57) ABSTRACT

The present invention relates to organic molecules capable of modulating tyrosine kinase signal transduction in order to regulate, modulate and/or inhibit abnormal cell proliferation.

7 Claims, 3 Drawing Sheets

Scheme 1

Scheme 2

Scheme 3

KINASE INHIBITORS FOR THE TREATMENT OF DISEASE

BACKGROUND OF THE INVENTION

1. Field of the Invention

The present invention relates to prodrugs of compounds capable of modulating, regulating and/or inhibiting tyrosine kinase signal transduction. The present invention is also directed to methods of regulating, modulating or inhibiting tyrosine kinases, whether of the receptor or non-receptor class, for the prevention and/or treatment of disorders related to unregulated tyrosine kinase signal transduction, including cell growth, metabolic, and blood vessel proliferative disorders.

2. Description of the Related Art

Protein tyrosine kinases (PTKs) comprise a large and diverse class of proteins having enzymatic activity. The PTKs play an important role in the control of cell growth and differentiation.

For example, receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic homeostasis, and responses to the extracellular microenvironment).

With respect to receptor tyrosine kinases, it has been shown also that tyrosine phosphorylation sites function as high-affinity binding sites for SH2 (src homology) domains of signaling molecules. Several intracellular substrate proteins that associate with receptor tyrosine kinases (RTKs) have been identified. They may be divided into two principal groups: (1) substrates which have a catalytic domain; and (2) substrates which lack such domain but serve as adapters and associate with catalytically active molecules. The specificity of the interactions between receptors or proteins and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Aberrant expression or mutations in the PTKs have been shown to lead to either uncontrolled cell proliferation (e.g. malignant tumor growth) or to defects in key developmental processes. Consequently, the biomedical community has expended significant resources to discover the specific biological role of members of the PTK family, their function in differentiation processes, their involvement in tumorigenesis and in other diseases, the biochemical mechanisms underlying their signal transduction pathways activated upon ligand stimulation and the development of novel drugs.

Tyrosine kinases can be of the receptor-type (having extracellular, transmembrane and intracellular domains) or the non-receptor type (being wholly intracellular).

The RTKs comprise a large family of transmembrane receptors with diverse biological activities. The intrinsic function of RTKs is activated upon ligand binding, which results in phophorylation of the receptor and multiple cellular substrates, and subsequently in a variety of cellular responses.

At present, at least nineteen (19) distinct RTK subfamilies have been identified. One RTK subfamily, designated the HER subfamily, is believed to be comprised of EGFR, HER2, HER3 and HER4. Ligands to the Her subfamily of receptors include epithelial growth factor (EGF), TGF-α, amphiregulin, HB-EGF, betacellulin and heregulin.

A second family of RTKs, designated the insulin subfamily, is comprised of the INS-R, the IGF-1R and the IR-R. A third family, the "PDGF" subfamily includes the PDGF α and β receptors, CSFIR, c-kit and FLK-II. Another subfamily of RTKs, identified as the FLK family, is believed to be comprised of the Kinase insert Domain-Receptor fetal liver kinase-1 (KDR/FLK-1), the fetal liver kinase 4 (FLK-4) and the fms-like tyrosine kinase 1 (flt-1). Each of these receptors was initially believed to be receptors for hematopoietic growth factors. Two other subfamilies of RTKs have been designated as the FGF receptor family (FGFR1, FGFR2, FGFR3 and FGFR4) and the Met subfamily (c-met and Ron).

Because of the similarities between the PDGF and FLK subfamilies, the two subfamilies are often considered together. The known RTK subfamilies are identified in Plowman et al, 1994, DN&P 7(6): 334–339, which is incorporated herein by reference.

The non-receptor tyrosine kinases represent a collection of cellular enzymes which lack extracellular and transmembrane sequences. At present, over twenty-four individual non-receptor tyrosine kinases, comprising eleven (11) subfamilies (Src, Frk, Btk, Csk, Abl, Zap70, Fes/Fps, Fak, Jak, Ack and LIMK) have been identified. At present, the Src subfamily of non-receptor tyrosine kinases is comprised of the largest number of PTKs and include Src, Yes, Fyn, Lyn, Lck, Blk, Hck, Fgr and Yrk. The Src subfamily of enzymes has been linked to oncogenesis. A more detailed discussion of non-receptor tyrosine kinases is provided in Bolen, 1993, Oncogen 8: 2025–2031, which is incorporated herein by reference.

Many of the tyrosine kinases, whether an RTK or non-receptor tyrosine kinase, have been found to be involved in cellular signaling pathways leading to cellular signal cascades leading to pathogenic conditions, including cancer, psoriasis and hyper immune response.

In view of the surmised importance of PTKs to the control, regulation and modulation of cell proliferation the diseases and disorders associated with abnormal cell proliferation, many attempts have been made to identify receptor and non-receptor tyrosine kinase "inhibitors" using a variety of approaches, including the use of mutant ligands (U.S. Pat. No. 4,966,849), soluble receptors and antibodies (PCT Application No. WO 94/10202; Kendall & Thomas, 1994, Proc. Nat'l Acad. Sci 90: 10705–09; Kim, et al, 1993, Nature 362: 841–844), RNA ligands (Jellinek, et al, Biochemistry 33: 10450–56); Takano, et al, 1993, Mol. Bio. Cell 4:358A; Kinsella, et al, 1992, Exp. Cell Res. 199: 56–62; Wright, et al, 1992, J. Cellular Phys. 152: 448–57) and tyrosine kinase inhibitors (PCT Application Nos. WO 94/03427; WO 92/21660; WO 91/15495; WO 94/14808;

U.S. Pat. No. 5,330,992; Mariani, et al, 1994, Proc. Am. Assoc. Cancer Res. 35: 2268).

More recently, attempts have been made to identify small molecules which act as tyrosine kinase inhibitors. For example, bis monocyclic, bicyclic or heterocyclic aryl compounds (PCT Application No. WO 92/20642), vinyleneazaindole derivatives (PCT Application No. WO 94/14808) and 1-cyclopropyl-4-pyridyl-quinolones (U.S. Pat. No. 5,330,992) have been described generally as tyrosine kinase inhibitors. Styryl compounds (U.S. Pat. No. 5,217,999), styryl-substituted pyridyl compounds (U.S. Pat. No. 5,302,606), certain quinazoline derivatives (EP Application No. 0 566 266 A1), seleoindoles and selenides (PCT Application No. WO 94/03427), tricyclic polyhydroxylic compounds (PCT Application No. WO 92/21660) and benzylphosphonic acid compounds (PCT Application No. WO 91/15495) have been described as compounds for use as tyrosine kinase inhibitors for use in the treatment of cancer.

The identification of effective small compounds which specifically inhibit signal transduction by modulating the activity of receptor and non-receptor tyrosine kinases to regulate and modulate abnormal or inappropriate cell proliferation is therefore desirable and one object of this invention.

Finally, certain small compounds are disclosed in U.S. Pat. Nos. 5,792,783; 5,834,504; 5,883,113; 5,883,116 and 5,886,020 as useful for the treatment of diseases related to unregulated TKS transduction. These patents are hereby incorporated by reference in its entirety for the purpose of disclosing starting materials and methods for the preparation thereof, screens and assays to determine a claimed compound's ability to modulate, regulate and/or inhibit cell proliferation, indications which are treatable with said compounds, formulations and routes of administration, effective dosages, etc.

As background to the present invention the concept of prodrugs which is well known in the art. Prodrugs are derivatives of drugs, which after administration undergo conversion to the physiologically active species. This conversion may be due caused by hydrolysis in the physiological environment, or be due to enzymatic hydrolysis. The following literature is cited: Design of Pro-drugs (Bundgaard H. ed.) 1985 Elsevier Science Publishers B.V. (Biomedical Devision), Chapter 1; Design of Prodrugs:Bioreversible derivatives for various functional groups and chemical entities (Hans Bundgaard); Bundgaard et al. Int.J. of Pharmaceutics 22 (1984) 45–56 (Elsevier); Bundgaard et al Int. J. of Pharmaceutics 29 (1986) 19–28 (Elsevier); Bundgaard et al.J.Med. Chem. 32 (1989) 2503–2507 Chem. Abstracts 95, 138493f (Bungaard et al.); Chem. Abstracts 95, 138592n (Bundgaard et al.); Chem Abstracts 110, 57664p (Alminger et al.) Chem. Abstracts 115, 64029s (Buur et al.); Chem Abstracts 115, 189582y (Hansen et al.); Chem.Abstracts 117, 14347q (Bundgaard et al.); Chem. Abstracts 117, 55790x (Jensen et al.); and Chem Abstracts 123, 17593b (Thomsen et al).

BRIEF DESCRIPTION OF THE DRAWING FIGURES

BRIEF SUMMARY OF THE INVENTION

Figure 1:
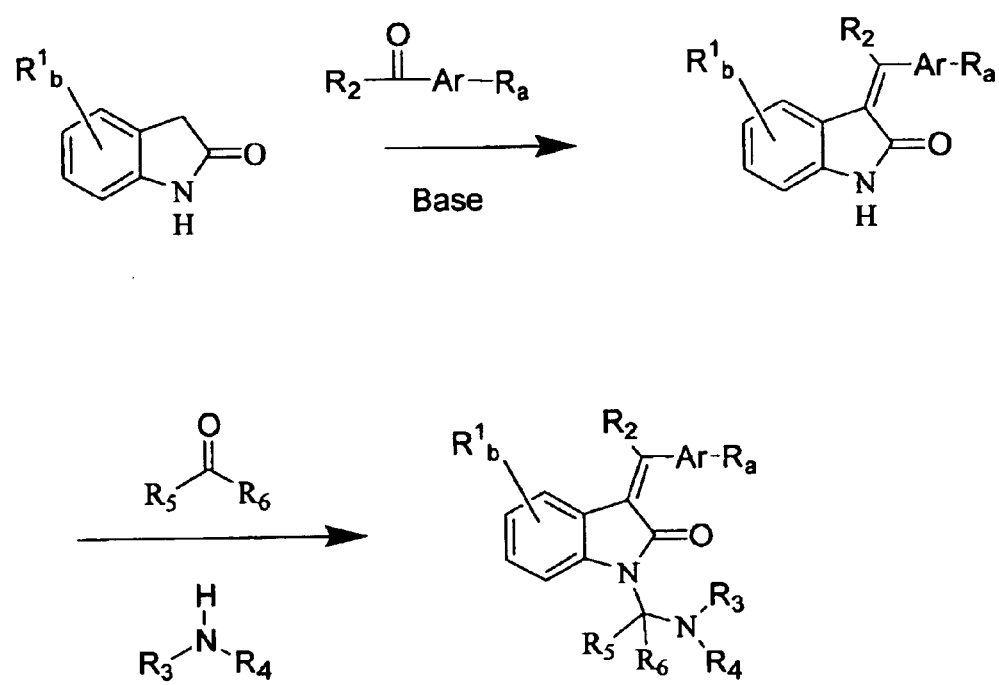
FIG. 1 shows the general scheme for the preparation of the compounds of Examples 2–6, 8 and 9.
Figure 2:
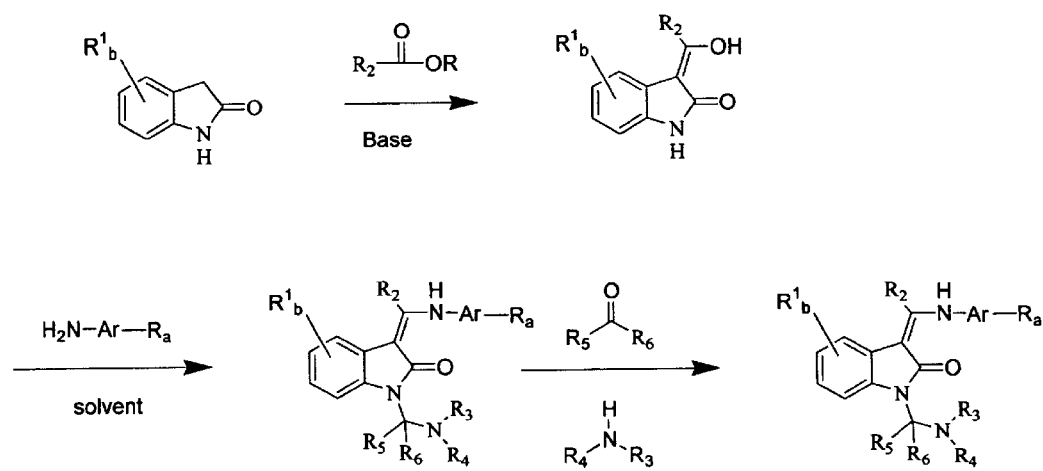
FIG. 2 shows the general scheme for the preparation of the compounds of Examples 12 and 13.
Figure 3:
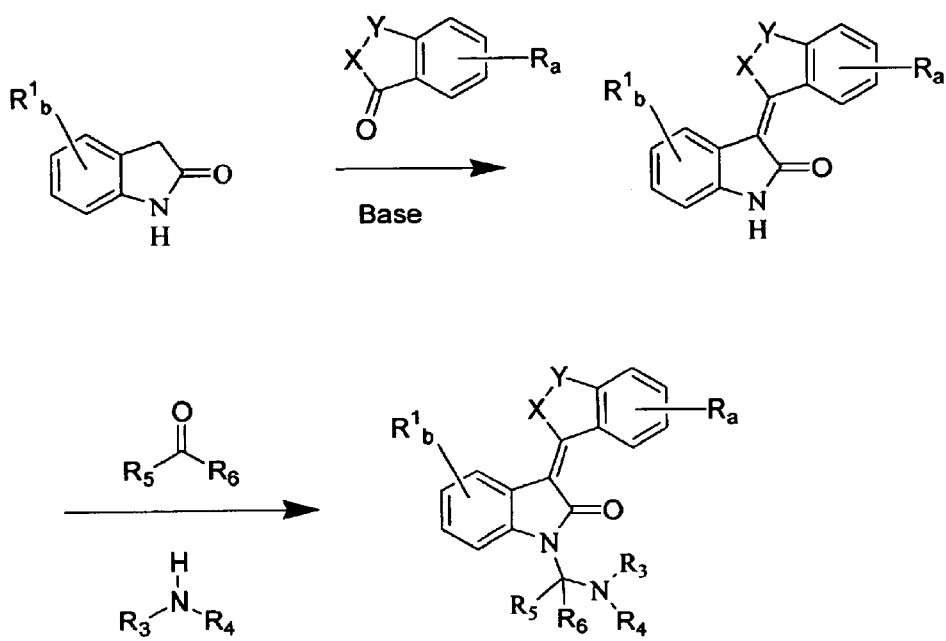
FIG. 3 shows the general scheme for the preparation of the compounds of Examples 15, 16, 19 and 21.

The present invention relates to organic molecules capable of modulating, regulating and/or inhibiting tyrosine kinase signal transduction. Such compounds are useful for the treatment of diseases related to unregulated TKS transduction, including cell proliferative diseases such as cancer, atherosclerosis, restenosis, metabolic diseases such as diabetes, inflammatory diseases such as psoriasis and chronic obstructive pulmonary disease, vascular proliferative disorders such as diabetic retinopathy, age-related macular degeneration and retinopathy of prematurity, autoimmune diseases and transplant rejection.

DETAILED DESCRIPTION OF THE INVENTION

In one illustrative embodiment, the compounds of the present invention have the formula I:

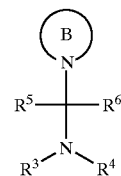

I wherein the fragment B represents a tyrosine kinase inhibitor or serine threonine kinase inhibitor containing a nitrogen atom capable of reacting with formaldehyde, a substituted aldehyde or substituted ketone and an amine to provide a compound of formula I and wherein;

$R^3$ and $R^4$ are independently selected from the group consisting of hydrogen, hydrocarbyl and substituted hydrocarbyl radicals, wherein said substituted hydrocarbyl may be substituted with heteroatoms selected from the group consisting of halogen, e.g. fluoro, chloro, bromo, or iodo, nitrogen, phosphorus, sulfur and oxygen, or $R^3$ and $R^4$ together with the nitrogen atom may form a cyclic ring, which ring may be substituted with said heteroatoms, e.g. $R^3$ and $R^4$ may be selected from the group consisting of hydrogen, alkyl, alkoxy, alkyloxyalkyl, aryl, aryloxy, alkylaryl and alkaryloxy; and $R^5$ and $R^6$ are independently selected from the group consisting of hydrogen, alkyl and aryl radicals. Preferably, $R^5$ and $R^6$ are hydrogen.

In a preferred embodiment the compounds of the present invention have the formula II or III:

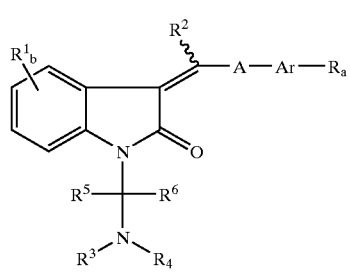

II

-continued

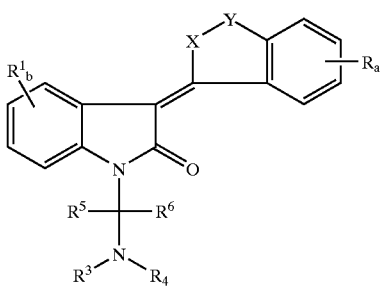

III wherein;

X is O or $C(R^2)_2$;

Y is $[C(R^2)_2]_c$;

A is $NR^2$ or absent;

$R^1$ is selected from the group consisting of halogen, hydroxy, $NO_2$, CN, hydrocarbyl and substituted hydrocarbyl radicals, wherein said substituted hydrocarbyl may be substituted with heteroatoms selected from the group consisting of halogen, e.g. fluoro, chloro, bromo, or iodo, nitrogen, phosphorus, sulfur and oxygen, e.g. $C_1$ to $C_4$ alkyl and aryl, e.g. phenyl, and when b is 1, $R^1$ is preferably chloro;

$R^2$ is selected from the group consisting of hydrogen, $C_1$ to $C_8$ alkyl, $(CR^8R^9)_d C(O)OR^{10}$, $COCH_3$, $CH_2CH_2OH$, $CH_2CH_2CH_2OH$ and phenyl; R is selected from the group consisting of halogen, hydrocarbyl and substituted hydrocarbyl radicals, wherein said substituted hydrocarbyl may be substituted with heteroatoms selected from the group consisting of halogen, e.g. fluoro, chloro, bromo, or iodo, nitrogen, phosphorus, sulfur and oxygen, e.g. R may be selected from the group consisting of halogen, $C_1$ to $C_8$ alkyl, $CF_3$, $OCF_3$, $OCF_2H$, $CH_2CN$, CN, $SR^2$, $(CR^8R^9)_d C(O)OR^2$, $(CR^8R^9)_d C(O)N(R^2)_2$, $(CR^8R^9)_d OR^2$, HNC(O)$R^2$, HN—C(O)$OR^2$, $(CR^8R^9)_d N(R^2)_2$, $SO_2(CR^8R^9)_d N(R^2)_2$, $OP(O)(OR^2)_2$, $OC(O)OR^2$, $OCH_2O$, HN—CH=CH, —N(COR$^2$)CH$_2$CH$_2$, HC=N—NH, N=CH—S, $O(CR^8R^9)_e R^7$, $(CR^8R^9)_d R^7$ and —$NR_2(CR^8R^9)_e R^7$ wherein $R^7$ is selected from the group consisting of halogen, 3-fluoropyrrolidinyl, 3-fluoropiperidinyl, 2-pyridinyl, 3-pyridinyl, 4-pyridinyl, 3-pyrrolinyl, pyrrolidinyl, piperidinyl, methyl isonipecotate, N-(2-methoxyethyl)-N-methylamyl, 1,2,3,6-tetrahydropyridinyl, morpholinyl, hexamethyleneiminyl, piperazinyt-2-one, piperazinyl, N-(2-methoxyethyl)ethylaminyl, thiomorpholinyl, heptamethyleneiminyl, 1-piperazinylcarboxal dehyde, 2,3,6,7-tetrahydro-(1H)-1,4-diazepinyl-5(4H)-one, N-methylhomopiperazinyl, (3-dimethylamino) pyrrolidinyl, N-(2-methoxyethyl)-N-propylaminyl, isoindolinyl, nipecotamidinyl, isonipecotamidinyl, 1-acetylpiperazinyl, 3-acetamidopyrrolidinyl, trans-decahydroisoquinolinyl, cis-decahydroisoquinolinyl, N-acetylhomopiperazinyl, 3-(diethylamino) pyrrolidinyl, 1,4-dioxa-8-azaspiro[4.5]decaninyl, 1-(2-methoxyethyl)-piperazinyl, 2-pyrrolidin-3-ylpyridinyl, 4-pyrrolidin-3-ylpyridinyl, 3-(methylsulfonyl) pyrrolidinyl, 3-picolylmethylaminyl, 2-(2-methylaminoethyl)pyridinyl, 1-(2-pyrimidyl)-piperazinyl, 1-(2-pyrazinyl)-piperazinyl, 2-methylaminomethyl-1,3-dioxolane, 2-(N-methyl-2-aminoethyl)-1,3-dioxolane, 3-(N-acetyl-N-methylamino)pyrrolidinyl, 2-methoxyethylaminyl, tetrahydrofurfirylaminyl, 4-aminotetrahydropyran, 2-amino-1-methoxybutane, 2-methoxyisopropylaminyl, 1-(3-aminopropyl) imidazole, histamyl, N,N-diisopropylethylenediaminyl, 1-benzyl-3-aminopyrrolidyl 2-(aminomethyl)-5-methylpyrazinyl, 2,2-dimethyl-1,3-dioxolane-4-methanaminyl, (R)-3-amino-1-N-BOC-pyrrolidinyl, 4-amino-1,2,2,6,6-pentamethylpiperidinyl, 4-aminomethyltetrahydropyran, ethanolamine and alkyl-substituted derivatives thereof; provided said alkyl or phenyl radicals may be substituted with one or two halo, hydroxy or lower alkyl amino radicals;

wherein $R^8$ and $R^9$ may be selected from the group consisting of H, halogen, e.g. F, hydroxy, and $C_1$–$C_4$ alkyl or $CR^8R^9$ may represent a carbocyclic ring of from 3 to 6 carbons, preferably $R^8$ and $R^9$ are H or $CH_3$, preferably in the compounds of Formula III when a is 1, R is dimethyl amino and in the compounds of Formula II when a is 1, R is morpholonyl;

$R^3$, $R^4$, $R^5$ and $R^6$, are as defined above;

$R^{10}$ is hydrogen, $C_1$ to $C_8$ alkyl or arylalkyl;

a is 0 or an integer of from 1 to 3;

b is 0 or an integer of from 1 to 3;

c is an integer of from 1 to 2;

d is 0 or an integer of from 1 to 5 e is an integer of from 2 to 5 the wavy line represents a E or Z bond; and

Ar is selected from the group consisting of aryl, substituted aryl, heteroaryl, and substituted heteroaryl, wherein said substituted hydrocarbyl or said substituted heteroaryl may be substituted with heteroatoms selected from the group consisting of halogen, e.g. fluoro, chloro, bromo, or iodo, nitrogen, phosphorus, sulfur and oxygen, e.g. Ar may be selected from the group consisting of monocyclic and bicyclic aryl and heteroaryl, including both fused and non-fused dicyclic aryl or heteroaryl, e.g. phenyl, naphthyl, pyridyl, pyrrolyl, furyl, thienyl, etc. and substituted derivatives thereof; and pharmaceutically acceptable salts thereof. Preferably, Ar is a monocyclic aryl or heteroaryl, e.g., phenyl or pyrrolyl.

Preferably $R^5$ and $R^6$ are hydrogen.

Preferably $R^3$ is H and $R^4$ is selected from the group consisting of alkyl, e.g. n-butyl, or alkyloxyalkyl, e.g. methyloxypropyl, or $R^3$ and $R^4$, together with the nitrogen atom forms a cyclic ring having 5 or 6 members, e.g., a 6 member ring, which may include an enchained oxygen or nitrogen atom, e.g. $R^3$ and $R^4$ may, together with the nitrogen atom may be morpholinyl or piperidinyl and said morpholinyl or said piperidinyl ring may be substituted with one or more lower alkyl groups, e.g., methyl.

Preferably, X is O and Y is $CH_2$ and R may be di(lower) alkyl amino, e.g., dimethyl amino.

Preferably, Ar is phenyl or pyrrolyl and R may be lower alkyl, e.g., methyl, or morpholinyl.

In one preferred embodiment of the invention, the $R^3$ and $R^4$ together with the nitrogen atom form a cyclic ring having from 3 to 8, e.g., 5 or 6, members and more preferably said cyclic ring includes an enchained oxygen atom or a second nitrogen atom. That is, $R^3$ and $R^4$ together with the nitrogen atom may be pyrrolidinyl, piperidinyl, piperazinyl or morpholinyl.

In another preferred embodiment $R^3$ is hydrogen and $R^4$ is alkyl or alkyloxyalkyl.

In one preferred embodiment of formula II A is —NH—, Ar is

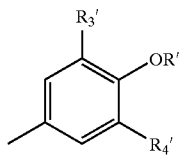

IV wherein
R$_3$', and R$_4$' are each independently selected from the group consisting of hydrogen, alkyl, alkoxy, aryl, aryloxy, alkaryl, alkaryloxy, halogen, trihalomethyl, S(O)R$^2$, SO$_2$(R$^2$)$_2$, SO$_3$R$^2$, SR$^2$, NO$_2$, N(R$^2$)$_2$, OH, CN, C(O)R$^2$, OC(O)R$^2$, NHC(O)R$^2$, (CH$_2$)$_d$CO$_2$R$^2$, and (CH$_2$)$_d$CON(R$^2$)$_2$;

R' is hydrogen, alkyl, aryl, alkylaryl, haloalkyl, (CR$^8$R$^9$)$_d$C(O)OR$^2$, (CR$^8$R$^9$)$_e$OR$^2$, or (CR$^8$R$^9$)$_e$N(R$^2$)$_2$, or (CR$^8$R$^9$)$_e$R$^7$, wherein d, e, R$^2$, R$^7$, R$^8$ and R$^9$ are as defined above.

In another preferred embodiment of formula II A is —NH—, Ar is

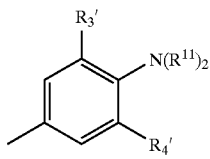

V wherein R$_3$' and R$_4$', are as defined above, R$^{11}$ is R$^1$ or R$^{11}$ taken together with the nitrogen atom may be a 5 or 6 membered ring which may have an enchained oxygen atom or a second nitrogen atom, for example morpholinyl, piperidinyl piperzinyl, etc.

In yet another preferred embodiment of formula II, A is absent, Ar is a five membered heteroaryl ring selected from the group consisting of furyl, thiophene, pyrrole, 2,4-dimethylpyrrole, 2,4-dimethyl-3-pyrrole-propionic acid, pyrazole, imidazole, 1,2,3-triazole, 1,2,4-triazole, oxazole, isoxazole, thiazole, isothiazole, 2-sulfonylfuran, 4-alkylfuran, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-thiadiazole, 1,2,4-thiadiazole, 1,2,5-thiatriazole, and tetrazole, optionally substituted at one or more positions with R$^2$, O(CR$^8$R$^9$)$_e$N(R$^2$)$_2$, (CR$^8$R$^9$)$_d$N(R$^2$)$_2$ or NR$^2$(CR$^8$R$^9$)$_e$N(R$^2$)$_2$ (CR$^8$R$^9$)$_d$C(O)OR$^2$, O(CR$^8$R$^9$)$_e$R$^7$ and (CR$^8$R$^9$)$_d$R$^7$ and NR$^2$(CR$^8$R$^9$)$_e$R$^7$, wherein d, e, R$^2$, R$^7$, R$^8$ and R$^9$ are as defined above.

In yet another preferred embodiment of formula II A is —NH—, Ar is a five membered heteroaryl ring selected from the group consisting of furyl, thiophene, pyrrole, 2,4-dimethylpyrrole, pyrazole, imidazole, 1,2,3-triazole, 1,2,4-triazole, oxazole, isoxazole, thiazole, isothiazole, 2-sulfonylfuran, 4-alkylfuran, 1,2,3-oxadiazole, 1,2,4-oxadiazole, 1,2,5-oxadiazole, 1,3,4-oxadiazole, 1,2,3,4-oxatriazole, 1,2,3,5-oxatriazole, 1,2,3-thiadiazole, 1,2,4-thiadiazole, 1,2,5-thiatriazole, and tetrazole, optionally substituted at one or more positions with with R$^2$, O(CR$^8$R$^9$)$_e$N(R$^2$)$_2$, (CR$^8$R$^9$)$_d$N(R$^2$)$_2$, NR$^2$(CR$^8$R$^9$)$_e$N(R$^2$)$_2$, (CR$^8$R$^9$)$_d$C(O)OR$^2$, O(CR$^8$R$^9$)$_e$R$^7$, (CR$^8$R$^9$)$_d$R$^7$ and NR$^2$(CR$^8$R$^9$)$_e$R$^7$ and wherein d, e, R$^2$, R$^7$, R$^8$ and R$^9$ are as defined above.

In a preferred embodiment of formula II; X is O or CH$_2$;
Y is [C(R$^2$)$_2$]$_c$;
R$^1$ is selected from the group consisting of halogen, hydroxy, C$_1$ to C$_4$ alkyl;
R$^2$ is selected from the group consisting of hydrogen, C$_1$ to C$_8$ alkyl, (CR$^8$R$^9$)$_d$C(O)OR$^{10}$;
R is selected from the group consisting of halogen, C$_1$ to C$_8$ alkyl, CF$_3$, OCF$_3$, OCF$_2$H, (CR$^8$R$^9$)$_d$C(O)OR$^2$, (CR$^8$R$^9$)$_d$C(O)N(R$^2$)$_2$, HNC(O)R$^2$, HN—C(O)OR$^2$, (CR$^8$R$^9$)$_d$N(R$^2$)$_2$, SO$_2$(CR$^8$R$^9$)$_d$N(R$^2$)$_2$, O(CR$^8$R$^9$)$_e$R$^7$ and (CR$^8$R$^9$)$_d$R$^7$, —NR$^2$(CR$^8$R$^9$)R$^7$ wherein d, e, R$^2$, R$^7$, R$^8$ and R$^9$ are as defined above.

The present invention is further directed to pharmaceutical compositions comprising a pharmaceutically effective amount of the above-described compounds and a pharmaceutically acceptable carrier or excipient. Such a composition is believed to modulate signal transduction by a tyrosine kinase, either by inhibition of catalytic activity, affinity to ATP or ability to interact with a substrate.

More particularly, the compositions of the present invention may be included in methods for treating diseases comprising proliferation, fibrotic or metabolic disorders, for example cancer, fibrosis, psoriasis, atherosclerosis, arthritis, and other disorders related to abnormal vasculogenesis and/or angiogenesis, such as diabetic retinopathy.

"Pharmaceutically acceptable salt" refers to those salts which retain the biological effectiveness and properties of the free bases and which are obtained by reaction with inorganic acids such as hydrochloric acid, hydrobromic acid, sulfuric acid, nitric acid, phosphoric acid, methanesulfonic acid, ethanesulfonic acid, p-toluenesulfonic acid, salicylic acid and the like.

"Alkyl" refers to a straight-chain, branched or cyclic saturated aliphatic hydrocarbon. Preferably, the alkyl group has 1 to 12 carbons. More preferably, it is a lower alkyl of from 1 to 7 carbons, most preferably 1 to 4 carbons. Typical alkyl groups include methyl, ethyl, propyl, isopropyl, butyl, isobutyl, tertiary butyl, pentyl, hexyl and the like. The alkyl group may be optionally substituted with one or more substituents are selected from the group consisting of hydroxyl, cyano, alkoxy, =O, =S, NO$_2$, halogen, dimethyl amino, and SH.

"Alkenyl" refers to a straight-chain, branched or cyclic unsaturated hydrocarbon group containing at least one carbon-carbon double bond. Preferably, the alkenyl group has 1 to 12 carbons. More preferably it is a lower alkenyl of from 1 to 7 carbons, most preferably 1 to 4 carbons. The alkenyl group may be optionally substituted with one or more substituents selected from the group consisting of hydroxyl, cyano, alkoxy, =O, =S, NO$_2$, halogen, dimethyl amino, and SH.

"Alkynyl" refers to a straight-chain, branched or cyclic unsaturated hydrocarbon containing at least one carbon-carbon triple bond. Preferably, the alkynyl group has 1 to 12 carbons. More preferably it is a lower alkynyl of from 1 to 7 carbons, most preferably 1 to 4 carbons. The alkynyl group may be optionally substituted with one or more substituents selected from the group consisting of hydroxyl, cyano, alkoxy, =O, =S, NO$_2$, halogen, dimethyl amino, and SH.

"Alkoxyl" refers to an "O-alkyl" group.

"Aryl" refers to an aromatic group which has at least one ring having a conjugated pi electron system and includes carbocyclic aryl, heterocyclic aryl and biaryl groups. The aryl group may be optionally substituted with one or more substituents selected from the group consisting of halogen, trihalomethyl, hydroxyl, SH, OH, NO$_2$, amine, thioether, cyano, alkoxy, alkyl, and amino.

"Alkaryl" refers to an alkyl that is covalently joined to an aryl group. Preferably, the alkyl is a lower alkyl.

"Carbocyclic aryl" refers to an aryl group wherein the ring atoms are carbon.

"Heterocyclic aryl" refers to an aryl group having from 1 to 3 heteroatoms as ring atoms, the remainder of the ring atoms being carbon. Heteroatoms include oxygen, sulfur, and nitrogen. Thus, heterocyclic aryl groups include furanyl, thienyl, pyridyl, pyrrolyl, N-lower alkyl pyrrolo, pyrimidyl, pyrazinyl, imidazolyl and the like.

"Hydrocarbyl" refers to a hydrocarbon radical having only carbon and hydrogen atoms. Preferably, the hydrocarbyl radical has from 1 to 20 carbon atoms, more preferably from 1 to 12 carbon atoms and most preferably from 1 to 7 carbon atoms.

"Substituted hydrocarbyl" refers to a hydrocarbyl radical wherein one or more, but not all, of the hydrogen and/or the carbon atoms are replaced by a halogen, nitrogen, oxygen, sulfur or phosphorus atom or a radical including a halogen, nitrogen, oxygen, sulfur or phosphorus atom, e.g. fluoro, chloro, cyano, nitro, hydroxyl, oxa, oxo, phosphate, thiol, etc.

"Amide" refers to —C(O)—NH—R, wherein R is alkyl, aryl, alkylaryl or hydrogen.

"Thioamide" refers to —C(S)—NH—R, wherein R is alkyl, aryl, alkylaryl or hydrogen.

"Amine" refers to a —N(R')R" group, wherein R' and R" are independently selected from the group consisting of alkyl, aryl, and alkylaryl.

"Thioether" refers to —S—R, wherein R is alkyl, aryl, or alkylaryl.

"Sulfonyl" refers to —S(O)$_2$—R, where R is aryl, C(CN) =C-aryl, CH$_2$CN, alkyaryl, sulfonamide, NH-alkyl, NH-alkylaryl, or NH-aryl.

In particular the compounds of the present invention are selected from the compounds of Table 1–Table 3, below.

TABLE 1

Substituted 1-Aminomethyl-3-(1H-pyrrol-2-ylmethylene)-1,3-dihydro-indol-2-one Analogs

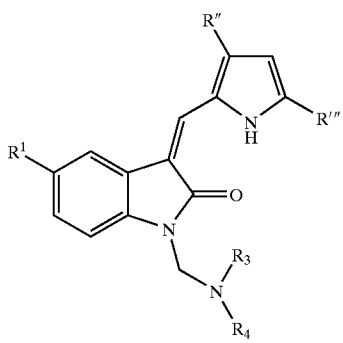

| Example # | R$^1$ | NR$_3$R$_4$ | R" | R''' |
|---|---|---|---|---|
| 2 | H | N(CH$_2$)$_5$ | H | H |
| 3 | H | N(CH$_2$)$_2$O(CH$_2$)$_2$ | H | H |
| 4 | H | N(CH$_2$)$_2$N(CH$_3$)(CH$_2$)$_2$ | H | H |
| 5 | H | NHCH$_2$CH$_2$CH$_2$OCH$_3$ | H | H |
| 6 | H | NHCH$_2$CH$_2$CH$_2$CH$_3$ | H | H |
| 8 | 5-Cl | N(CH$_2$)$_5$ | CH$_3$ | CH$_3$ |
| 9 | 5-Cl | N(CH$_2$)$_2$O(CH$_2$)$_2$ | CH$_3$ | CH$_3$ |

TABLE 2

Substituted 1-Aminomethyl-3-[(4-morpholin-4-yl-phenylamino)-methylene]-1,3-dihydro-indol-2-one Analogs

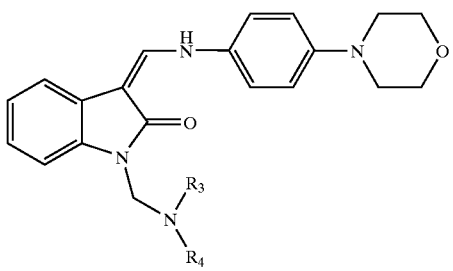

| Example # | NR$_3$R$_4$ |
|---|---|
| 12 | N(CH$_2$)$_5$ |
| 13 | N(CH$_2$)$_2$O(CH$_2$)$_2$ |

TABLE 3

Substituted 1-Aminomethyl-3-(3H-isobenzofuran-1-ylidene)-1,3-dihydro-indol-2-one Analogs

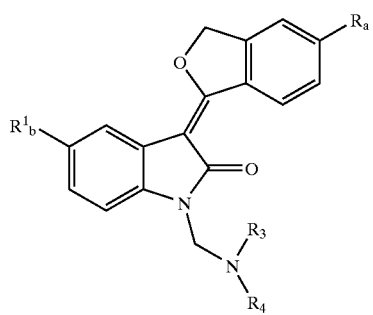

| Example # | R$^1$$_b$ | Ra | NR$_3$R$_4$ |
|---|---|---|---|
| 15 | H | H | N(CH$_2$)$_5$ |
| 16 | H | H | N(CH$_2$)$_2$O(CH$_2$)$_2$ |
| 19 | H | N(CH$_3$)$_2$ | N(CH$_2$)$_5$ |
| 21 | 5-Cl | N(CH$_3$)$_2$ | N(CH$_2$)$_5$ |

Note in Examples 15, 16 and 19, b is 0, therefore R$^1$ is given as H. In Examples 15 and 16 a is 0, therefore R is given as H.

The present invention relates to compounds capable of regulating and/or modulating tyrosine kinase signal transduction and more particularly receptor and non-receptor tyrosine kinase signal transduction.

Receptor tyrosine kinase mediated signal transduction is initiated by extracellular interaction with a specific growth factor (ligand), followed by receptor dimerization, transient stimulation of the intrinsic protein tyrosine kinase activity and phosphorylation. Binding sites are thereby created for intracellular signal transduction molecules and lead to the formation of complexes with a spectrum of cytoplasmic signaling molecules that facilitate the appropriate cellular response (e.g., cell division, metabolic effects and responses to the extracellular microenviroment).

It has been shown that tyrosine phosphorylation sites in growth factor receptors function as high-affinity binding sites for SH2 (src homology) domains of signaling molecules. Several intracellular substrate proteins that associate with receptor tyrosine kinases have been identified. They may be divided into two principal groups: (1) substrates which have a catalytic domain; and (2) substrates which lack such domain but serve as adapters and associate with catalytically active molecules. The specificity of the interactions between receptors and SH2 domains of their substrates is determined by the amino acid residues immediately surrounding the phosphorylated tyrosine residue. Differences in the binding affinities between SH2 domains and the amino acid sequences surrounding the phosphotyrosine residues on particular receptors are consistent with the observed differences in their substrate phosphorylation profiles. These observations suggest that the function of each receptor tyrosine kinase is determined not only by its pattern of expression and ligand availability but also by the array of downstream signal transduction pathways that are activated by a particular receptor. Thus, phosphorylation provides an important regulatory step which determines the selectivity of signaling pathways recruited by specific growth factor receptors, as well as differentiation factor receptors.

Tyrosine kinase signal transduction results in, among other responses, cell proliferation, differentiation and metabolism. Abnormal cell proliferation may result in a wide array of disorders and diseases, including the development of neoplasia such as carcinoma, sarcoma, leukemia, glioblastoma, hemangioma, psoriasis, arteriosclerosis, arthritis and diabetic retinopathy (or other disorders related to uncontrolled angiogenesis and/or vasculogenesis, e.g. macular degeneration).

This invention is therefore directed to compounds which regulate, modulate and/or inhibit tyrosine kinase signal transduction by affecting the enzymatic activity of the RTKs and/or the non-receptor tyrosine kinases and interfering with the signal transduced by such proteins. More particularly, the present invention is directed to compounds which regulate, modulate and/or inhibit the RTK and/or non-receptor tyrosine kinase mediated signal transduction pathways as a therapeutic approach to cure many kinds of solid tumors, including but not limited to carcinoma, sarcoma, leukemia, erythroblastoma, glioblastoma, meningioma, astrocytoma, melanoma and myoblastoma. Indications may include, but are not limited to brain cancers, bladder cancers, ovarian cancers, gastric cancers, pancreas cancers, colon cancers, blood cancers, lung cancers and bone cancers.

Chemical Stability

The chemical stability of Example 12 of the invention has been studied using buffers at pH 1, pH 3 and pH 7. Example 12 prepared in acetonitrile at 200 µg/mL and diluted to 20 µg/mL in buffers at pH 1, pH 3 and pH 7. Example 12 was measured to have a half-life ($t_{1/2}$) of approximately 20 hours at pH 3 and 38 hours at pH 1. The half-life ($t_{1/2}$) of Example 12 at pH 7.4 was less than 30 minutes.

Biological data for the compounds of the present invention was generated by use of the following assays.

VEGF Stimulated $Ca^{++}$ Signal In vitro

Automated FLIPR (Fluorometric Imaging Plate Reader) technology was used to screen for inhibitors of VEGF induced increases in intracellular calcium levels in fluorescent dye loaded endothelial cells. HUVEC (human umbilical vein endothelial cells) (Clonetics) were seeded in 96-well fibronectin coated black-walled plates overnight at 37° C./5%$CO_2$. Cells were loaded with calcium indicator Fluo-4 for 45 minutes at 37° C. Cells were washed 4 times (Original Cell Wash, Labsystems) to remove extracellular dye. Test compounds were reconstituted in 100% DMSO and added to the cells to give a final DMSO concentration of 0.1%. For screening, cells were pre-incubated with test agents for 30 minutes, at a single concentration (10 µM) or at concentrations ranging from 0.01 to 10.0 µM followed by VEGF stimulation (5 ng/mL). Changes in fluorescence at 516 nm were measured simultaneously in all 96 wells using a cooled CCD camera. Data were generated by determining max-min fluorescence levels for unstimulated, stimulated, and drug treated samples. $IC_{50}$ values for test compounds were calculated from % inhibition of VEGF stimulated responses in the absence of inhibitor.

VEGFR2 Kinase Assay

The cytoplasmic domain of the human VEGF receptor (VEGFR-2) was expressed as a Hisfidine-tagged fusion protein following infection of insect cells using an engineered baculovirus. His-VEGFR-2 was purified to homogeneity, as determined by SDS-PAGE, using nickel resin chromatography. Kinase assays were performed in 96 well microtiter plates that were coated overnight with 30 µg of poly-Glu-Tyr (4:1) in 10 mM Phosphate Buffered Saline (PBS), pH 7.2–7.4. The plates were incubated with 1% BSA and then washed four times with PBS prior to starting the reaction. Reactions were carried out in 120 µL reaction volumes containing 3.6 µM ATP in kinase buffer (50 mM Hepes buffer pH 7.4, 20 mM $MgCl_2$, 0.1 mM $MnCl_2$ and 0.2 mM $Na_3VO_4$). Test compounds were reconstituted in 100% DMSO and added to the reaction to give a final DMSO concentration of 5%. Reactions were initiated by the addition 0.5 ng of purified protein. Following a ten minute incubation at 25° C., the reactions were washed four times with PBS containing 0.05% Tween-20. 100 µl of a monoclonal anti-phosphotyrosine antibody-peroxidase conjugate was diluted 1:10000 in PBS-Tween-20 and added to the wells for 30 minutes. Following four washes with PBS-Tween-20, 100 µl of O-phenylenediamine Dihydrochloride in Phosphate-citrate buffer, containing urea hydrogen peroxide, was added to the wells for 7 minutes as a colorimetric substrate for the peroxidase. The reaction was terminated by the addition of 100 µl of 2.5N $H_2SO_4$ to each well and read using a microplate ELISA reader set at 492 nm. $IC_{50}$ values for compound inhibition were calculated directly from graphs of optical density (arbitrary units) versus compound concentration following subtraction of blank values.

VEGF-induced Dermal Extravasation in Guinea Pig (Miles Assay)

Male Hartley guinea pigs (300–600 g) were anesthetized with isofluorane, sheared, and given a single dose of drug or the respective vehicle. The guinea pigs were dosed orally unless indicated otherwise in Table 3. Ten minutes prior to the end of drug treatment, guinea pigs were anesthetized with isofluorane, and 0.5% Evans blue dye (EBD) in PBS (13–15 mg/kg dose of EBD) was injected intravenously. After 5 minutes, triplicate intradermal injections of 100 ng $rhVEGF_{165}$ in 100 µl PBS and of 100 µl PBS alone were administered on the flank. After 20 minutes, each animal was euthanized with Pentosol, and the skin containing the intradermal injection sites was removed for image analysis.

Using an analog video camera coupled to a PC, an image of each trans-illuminated skin sample was captured, and the integrated optical density of each injection site was measured using ImagePro 4. For each skin sample, the difference between the mean optical density of the VEGF sites and mean optical density of the PBS sites is the measure of VEGF-induced EBD extravasation in that animal. These measured values were averaged per study group to determine the mean VEGF-induced EBD extravasation for each experimental condition, and the group means were then compared to assess inhibition of VEGF-induced EBD extravasation in the drug-treated groups relative to the vehicle-treated controls.

To determine the dose required for 50% inhibition (ID50), the percent inhibition data was plotted as a function of oral dose, using the 'best-fit' analysis within MicroSoft Excel software. The $ID_{50}$ value was verified visually by using the plotted data (horizontal line from 50% y value, at intersection with best-fit line drop vertical line to x axis (dose).

Laser-induced Choroidal Neovascularization (CNV) in Rat (CNV Assay)

CNV was induced and quantified in this model as previously described (Edelman and Castro. *Exp. Eye Res.* 2000; 71:523–533). On day 0, male Brown Norway rats (200–300 g) were anesthetized with 100 mg/kg Ketamine and 10 mg/kg Xylazine, and pupils were dilated with 1% Tropicamide. Using the blue-green setting of a Coherent Novus Argon Laser, 3 laser burns (90 mW for 0.1 s; 100 µm diameter) were given to each eye between the retinal vessels around the optic nerve head. Rats were dosed with test compounds in their indicated vehicles orally once daily.

On day 10, rats were sacrificed with 100% $CO_2$, and blood vessels were labeled by vascular perfusion with 10 mg/ml FITC-dextran (MW $2 \times 10^6$). Using an epifluorescence microscope (20×) coupled to a spot digital camera and a PC, images were obtained from the flat mounts of the RPE-choroid-sclera from each eye, and the area occupied by hyperfluorescent neovessels within each laser lesion was measured using ImagePro 4 software.

To determine the dose required for 50% inhibition ($ID_{50}$), the percent inhibition data was plotted as a function of oral dose, using the 'best-fit' analysis within MicroSoft Excel software. The $ID_{50}$ value was verified visually by using the plotted data (horizontal line from 50% y value, at intersection with best-fit line drop vertical line to x axis (dose).

The results of said assays are set forth in Table 4–6, below.

TABLE 4

VEGF Stimulated Ca++ Signal Assay and VEGF Kinase Assay Data

| Example # | VEGF Stimulated Ca++ Signal Assay $IC_{50}$ (nM) | VEGFR2 Kinase Assay $IC_{50}$ (nM) |
| --- | --- | --- |
| 11 | 294 | 260 |
| 12 | 432 | 478 |
| 13 | 722 | 3858 |
| 14 | 110 | |
| 15 | | |
| 16 | | |
| 18 | 22 | 31 |
| 19 | 120 | 133 |
| 20 | 33 | 22 |

TABLE 5

VEGF-induced Dermal Extravasation in Guinea Pig (Miles Assay) Results

| Example # | Vehicle | % Inhibition @ Dose (mg/Kg) | $ID_{50}$ |
| --- | --- | --- | --- |
| 11 | corn oil | 40% @ 75 mg/Kg | |
| 12 | corn oil | 88% @ 75 mg/Kg | 36 mg/Kg |
| 13 | corn oil | 35% @ 75 mg/Kg | |

TABLE 6

Rat Laser Choroidal Angiogenesis Assay Results

| Example # | Vehicle | % Inhibition @ Dose (mg/Kg) | $ID_{50}$ |
| --- | --- | --- | --- |
| 12 | corn oil | 94% @ 80 mg/Kg (sid) | 36 mg/Kg | sid = once daily dosing

The invention is further illustrated by the following non-limiting examples;

EXAMPLE 1

Preparation of Z-(1H-Pyrrol-2-ylmethylene)-1,3-dihydro-indol-2-one

A mixture of oxindole (137 mg, 1.03 mmol), pyrrole-2-carboxaldehyde (115.1 mg, 1.21 mmol) and piperidine (40 µL, 0.404 mmol) in 2.0 mL MeOH was heated at reflux for 3 h. The mixture was cooled in an ice bath and the solid which formed was collected by filtration to give the title compounds (208 mg, 96%) as a yellow solid.

EXAMPLE 2

Preparation of 1-Piperidin-1-ylmethyl-3-(1-H-pyrrol-2-ylmethylene)-1,3-dihydro-indol-2-one A solution of Z-(1H-Pyrrol-2-ylmethylene)-1,3-dihydro-indol-2-one (0.60 g, 2.85 mmol), paraformaldehyde (0.13 g, 4.28 mmol) and piperidine (0.24 g, 2.85 mmol) in EtOH (5 mL) was heated to 60–70° C. for 14 h. The reaction mixture was cooled to −20° C. for 1 h and the fine yellow solid present was collected by filtration. The solid collected was dried under vacuum to give the title compound as a yellow solid (0.68 g, 77%).

$^1$H NMR (500 MHz, $d_6$-DMSO) δ13.17 (br s, 1H), 7.81 (s, 1H), 7.67 (d, J=7.3 Hz, 1H), 7.37 (m, 1H), 7.22 (m, 1H), 7.18 (d, J=7.3 Hz, 1H), 7.06 (ddd, J=7.3, 7.3, 1.2 Hz, 1H), 6.88 (m, 1H), 6.37 (m, 1H), 4.58 (s, 2H), 2.54 (br s, 4H), 1.46 (m, 4H), 1.33 (br m, 2H).

EXAMPLE 3

Preparation of 1-Morpholin-4-ylmethyl-3-(1H-pyrrol-2-ylmethylene)-1,3-dihydro-indol-2-one A mixture of Z-(1H-Pyrrol-2-ylmethylene)-1,3-dihydro-indol-2-one (120 mg, 0.57 mmol), paraformaldehyde (32 mg, 1.1 mmol), and morpholine (62.2 µL, 0.71 mmol) in 8.0 mL of 20% dioxane in EtOH was heated at reflux for 19.5 h. The reaction mixture was concentrated and paraformaldehyde (10.0 mg, 0.33 mmol), morpholine (15 µL, 0.17 mmol) and EtOH (7 mL) was added. The reaction mixture refluxed for 24 h. The reaction mixture was cooled to room temperature and concentrated. The residue was dissolved in 15 mL of $CHCl_3$ and treated with activated charcoal. The resulting suspension was filtered and the filtrate concentrated. The residue was crystallization from ethyl acetate/hexane to give the title compound (88.0 mg, 50%) as a bright yellow solid.

$^1$H NMR (500 MHz, $d_6$-DMSO) δ13.03 (br s, 1H), 7.80 (s, 1H), 7.66 (d, J=7.3 Hz, 1H), 7.35 (br s, 1H), 7.19 (m, 2H), 7.05 (m, 1H), 6.86 (m, 1H), 6.35 (m, 1H), 4.56 (s, 2H), 3.52 (m, 4H), 2.53 (m, 4H).

EXAMPLE 4

Preparation of 1-(4-Methyl-piperazin-1-ylmethyl)-3-(1H-pyrrol-2-ylmethylene)-1,3-dihydro-indol-2-one A mixture of Z-(1H-Pyrrol-2-ylmethylene)-1,3-dihydro-indol-2-one (120 mg, 0.57 mmol), paraformaldehyde (17 mg, 0.57 mmol), and 1-methylpiperazine (63 μL, 0.57 mmol) in 4.0 mL EtOH was heated at reflux for 6.5 h. After standing at room temperature for 23 h, the mixture was concentrated to 3 mL solvent and 1 mL of hexane added. The resulting solution was cooled to 0° C. and the yellow solid which formed was collected by filtration. The solid collected was partitioned between 30 mL dilute HCl and 20 mL Ethyl acetate. The organic layer was removed and the aqueous layer washed with ethyl acetate (15 mL). The aqueous layer was made basic to pH 8 with saturated NaHCO$_3$ and extracted with ethyl acetate. The ethyl acetate layer was washed with H$_2$O, brine and dried with Na$_2$SO$_4$. The organic layer was concentrated and the residue was crystallized from ethyl acetate/hexane to give the title compound (38 mg, 21%) as a bright yellow solid.

$^1$H NMR (500 MHz, CDCl$_3$) δ13.35 (br s, 1H), 7.46 (d, J=7.6 Hz, 1H), 7.42 (s, 1H), 7.19 (dd, J=7.8, 7.6 Hz, 1H), 7.14 (br s, 1H), 7.06 (dd, J=7.6, 7.6 Hz, 1H), 7.02 (d, J=7.8 Hz, 1H), 6.75 (m, 1H), 6.36 (m, 1H), 4.57 (s, 2H), 2.69 (br s, 4H), 2.41 (br s, 4H), 2.24 (s, 3H).

EXAMPLE 5

Preparation of 1-[(3-Methoxy-propylamino)-methyl]-3-(1H-pyrrol-2-ylmethylene)-1,3-dihydro-indol-2-one A mixture of Z-(1H-Pyrrol-2-ylmethylene)-1,3-dihydro-indol-2-one (120.0 mg, 0.571 mmol), paraformaldehyde (17.1 mg, 0.571 mmol), and 3-methoxypropylamine (58.2 μL, 0.571 mmol) in 4.0 mL EtOH was heated at reflux for 6.5 h. The reaction mixture was cooled to room temperature and let stand for 22 h. The reaction mixture was filtered and the filter cake rinsed with 30% ethyl acetate in hexane. The filtrate was concentrated in vacuo and 4 ML of EtOH added. The reaction was refluxed an additional 19.5 h. The reaction mixture was cooled to room temperature and partitioned between 30 mL dilute HCl and 20 mL Ethyl acetate. The organic layer was removed and the aqueous layer washed with 15 mL ethyl acetate. The aqueous layer was made basic to pH 8 with saturated NaHCO$_3$ and extracted with ethyl acetate. The ethyl acetate layer was washed with H$_2$O, brine and dried over anhydrous Na$_2$SO$_4$. The ethyl acetate layer was filtered and then concentrated. The solid obtained (42.5 mg) was dissolved in CHCl$_3$ and purified by chromatography (silica gel, 1:1/hexane:acetone) to give the title compound (1.5 mg, 1%).

$^1$H NMR (500 MHz, CDCl$_3$) δ13.40 (br s, 1H), 7.50 (d, J=7.5 Hz, 1H), 7.44 (s, 1H), 7.21 (m, 1H), 7.16 (m, 1H), 7.07 (m, 1H), 6.95 (d, J=7.7 Hz, 1H), 6.77 (m, 1H), 6.38 (m, 1H), 4.81 (s, 2H), 3.37 (t, J=6.3 Hz, 2H), 3.24 (s, 3H), 2.69 (t, J=6.7 Hz, 2H), 1.72 (quintet, J=6.5 Hz, 2H).

EXAMPLE 6

Preparation of 1-Butylaminomethyl-3-(1H-pyrrol-2-ylmethylene)-1,3-dihydro-indol-2-one A mixture of Z-(1H-Pyrrol-2-ylmethylene)-1,3-dihydro-indol-2-one (120.0 mg, 0.571 mmol), paraformaldehyde (17.1 mg, 0.571 mmol), and butylamine (56.4 μL, 0.571 mmol) in 5.5 mL of EtOH was heated at reflux for 2.5 h. Then reaction mixture was treated with 2 mL of hexane was and then cooled to 0° C. The reaction mixture was then filtered to remove Z-(1H-Pyrrol-2-ylmethylene)-1,3-dihydro-indol-2-one. The filtrate was partitioned between dilute HCl and ethyl acetate. The organic layer was removed and the aqueous layer washed with 15 mL Ethyl acetate. The aqueous phase was made basic to pH 8 with saturated NaHCO$_3$ and extracted with ethyl acetate. The ethyl acetate layer was washed with H$_2$O, brine and dried over anhydrous Na$_2$SO$_4$. The solvent was removed in vacuo to give 58 mg of yellow oil. The oil was purified by chromatography (silica gel, 1:1/hexane:ethyl acetate) to give the title compound (51.6 mg, 31%) as a yellow solid.

$^1$H NMR (500 MHz, CDCl$_3$) δ13.41 (br s, 1H), 7.51 (d, J=7.5 Hz, 1H), 7.46 (s, 1H), 7.23 (m, 1H), 7.17 (br s, 1H), 7.09 (m, 1H), 6.96 (d, J=7.7 Hz, 1H), 6.78 (m, 1H), 6.39 (m, 1H), 4.83 (s, 2H), 2.61 (t, J=7.1 Hz, 2H), 1.43 (m, 2H), 1.29 (m, 2H), 0.86 (t, J=7.3 Hz, 3H).

EXAMPLE 7

Preparation of 5-chloro-3-(1H-pyrrol-2-yl-methylene)-1,3-dihydro-indol-2-one

A mixture of 5-chlorooxindole (6.98 g, 41.6 mmol), 3,5-dimethyl-1H-pyrrole-2-carboxaldehyde (5.12 g, 41.6 mmol) and piperidine (410 μL, 4.16 mmol) in 200 mL of EtOH was heated at reflux for 8 h. The reaction mixture was cooled to room temperature and filtered to give the title compound (4.50 g, 40%) as a red/orange solid.

EXAMPLE 8

Preparation of 5-Chloro-3-(3,5-dimethyl-1H-pyrrol-2-ylmethylene)-1-pieridin-1-ylmethyl-1,3-dihydro-indol-2-one A suspension of 5-chloro-3-(1H-pyrrol-2-yl-methylene)-1,3-dihydro-indol-2-one (260 mg, 0.96 mmol), piperidine (95 μL, 0.96 mmol) and paraformaldehyde (43 mg, 1.44 mmol) in 5 mL of dioxane and 5 mL of EtOH was heated to 80° C. for 15 h. The resulting solution was cooled to room temperature followed by cooling to −20° C. for 1 h. The solid which formed was collected by filtration and rinsed with EtOH (previously cooled to −20° C.). The solid collected was dried under vacuum to give the title compound (180 mg, 51%) as a yellow-orange solid.

EXAMPLE 9

Preparation of 5-Chloro-3-(3,5-dimethyl-1H-pyrrol-2-ylmethylene)-1-morpholin-4-ylmethyl-1,3-dihydro-indol-2-one A suspension of 5-chloro-3-(1H-pyrrol-2-yl-methylene)-1,3-dihydro-indol-2-one (120 mg, 0.44 mmol), morpholine (39 μL, 0.44 mmol) and paraformaldehyde (20 mg, 0.66 mmol) in 8 mL of dioxane and 2 mL of EtOH was heated to 80° C. for 15 h. The reaction mixture was cooled to room temperature and treated with morpholine (25 μL, 0.28 mmol) and paraformaldehyde (16 mg, 0.50 mmol) The reaction mixture was heated at 80° C. for 4 h. The reaction mixture was cooled to room temperature and partially concentrated under a nitrogen stream. The reaction mixture was cooled to −20° C. The solid which formed was collected by filtration and rinsed with EtOH (previously cooled to −20° C.). The solid collected was dried under vacuum to give the title compound (85 mg, 52%) as an orange solid.

EXAMPLE 10

Preparation of 3-Hydroxymethylene-1,3-dihydro-indol-2-one

To a slurry of oxindole (1,33 g, 10.0 mmol) and ethyl formate (2.42 mL, 30.0 mmol) was added 4.85 mL of 21 wt.

% NaOEt in EtOH. The thick solution was stirred for 30 min at room temperature and then heated at reflux for 30 min. The solution was acidified to pH=3 with 10% aqueous HCl and 5 mL H$_2$O was added. The solid which formed was filtered and rinsed with H$_2$O to give the title compound (1.34 g, 83%) as a pale yellow solid.

EXAMPLE 11

Preparation of 3-[(4-morpholinophenylamino)-methylene]-1,3-dihydro-indol-2-one

A solution of 4-morpholinoaniline (8.3 g, 51.5 mmol) in 100 mL of tetrahydrofuran was treated with 3-hydroxymethylene-1,3-dihydro-indol-2-one (5.5 g, 30.9 mmol) in one portion. The reaction mixture was heated at reflux for 3 h. The reaction mixture was concentrated. The residue was treated with 125 mL of ethyl acetate and the resulting suspension was heated at 40° C. for 2 h. The suspension was cooled to room temperature and the solid collected by suction filtration and washed with ethyl acetate. The solid obtained was dried under vacuum to give the title compound (10.1 g, 92%) as a yellow solid.

EXAMPLE 12

Preparation of 3-[(4-Morpholin-4-yl-phenylamino)-methylene]-1-piperidin-1-ylmethyl-1,3-dihydro-indol-2-one A solution of 3-[(4-morpholinophenylamino)-methylene]-1,3-dihydro-indol-2-one (17.3 g, 53.8 mmol) and paraformaldehyde (2.43 g, 80.9 mmol.) in 125 mL of EtOH was treated with piperidine (5.87 mL, 59.3 mmol). The reaction mixture was then heated at a reflux temperature for 5 hours during which time a yellow precipitate formed. The reaction mixture was allowed to cool to room temperature and the solid was collected by filtration and washed with EtOH and dried under vacuum to give the title compound (21.5 g, 95%) as a yellow solid.

EXAMPLE 13

Preparation of 1-Morpholin-4-ylmethyl-3-[(4-morpholin-4-yl-phenylamino)-methylene]-1,3-dihydro-indol-2-one A solution of 3-[(4-morpholinophenylamino)-methylene]-1,3-dihydro-indol-2-one (0.71 g, 2.21 mmol) and paraformaldehyde (0.10 g, 3.33 mmol.) in 8 mL of EtOH was treated with morpholine (213 μL, 2.44 mmol). The reaction mixture was then heated at a reflux temperature overnight during which time a yellow precipitate formed. The reaction mixture was allowed to cool to room temperature and the solid was collected by filtration and washed with EtOH and dried under vacuum to give the title compound (0.769 g, 83%) as a yellow solid.

EXAMPLE 14

Preparation of 3-(3H-isobenzofuran-1-ylidene)-1,3-dihydro-indol-2-one

To a suspension of sodium hydride (6.0 g, 150 mmol, 60% in mineral oil) in 300 mL DMF was added oxindole (10.0 g, 75.1 mmol) in 50 mL DMF over 8 min. After stirring for 15 min at room temperature, a solution of phthalide (13.1 g, 97.6 mmol) in 50 mL DMF was added over 1 min. The mixture was stirred for 1.25 h, then poured into 1100 mL H$_2$O. Addition of 4% aqueous HCl solution gave a yellow solid which was filtered and rinsed with H$_2$O to give the title compound (8.75 g, 47%).

$^1$H NMR (500 MHz, d$_6$-DMSO) δ10.41 (s, 1H), 9.65 (d, J=8.1 Hz, 1H), 7.83 (d, J=7.6 Hz, 1H), 7.65 (m, 2H), 7.55 (m, 1H), 7.10 (ddd, J=7.6, 7.6, 1.0 Hz, 1H), 6.95 (ddd, J=7.6, 7.6, 1.0 Hz, 1H), 6.81 (d, J=7.6 Hz, 1H), 5.81 (s, 2H).

EXAMPLE 15

Preparation of 3-(3H-Isobenzofuran-1-ylidene)-1-piperidin-1-ylmethyl-1,3-dihydro-indol-2-one A mixture of 3-(3H-isobenzofuran-1-ylidene)-1,3-dihydro-indol-2-one (4.32 g, 17.3 mmol), paraformaldehyde (0.99 g, 32.9 mmol), and piperidine (2.14 mL, 21.7 mmol) in 192 mL EtOH and 48 mL dioxane was heated at reflux for 18.5 h. The solution was concentrated in vacuo to a volume of 100 mL and then refluxed for 1 h to dissolve the precipitant. The mixture was allowed to cool to room temperature and the precipitate filtered to give the title compound (3.728 g) as a bright yellow solid. An additional 0.52 g of the title compound was obtained by crystallization of the filtrate from ethyl acetate. The two lots were combined to give 4.248 g (71%) of the title compound as a bright yellow solid.

$^1$H NMR (500 MHz, d$_6$-DMSO) δ9.67 (d, J=8.1 Hz, 1H), 7.90 (d, J=7.8 Hz, 1H), 7.68 (m, 2H), 7.58 (m, 1H), 7.18 (dd, J=7.8, 7.6 Hz, 1H), 7.12 (d, J=7.6 Hz, 1H), 7.03 (dd, J=7.6, 7.6 Hz, 1H), 5.83 (s, 2H), 4.50 (s, 2H), 2.52 (br s, 4H), 1.45 (m, 4H), 1,32 (br s, 2H).

EXAMPLE 16

Preparation of 3-(3H-Isobenzofuran-1-ylidene)-1-morpholin-4-ylmethyl-1,3-dihydro-indol-2-one A mixture of 3-(3H-isobenzofuran-1-ylidene)-1,3-dihydro-indol-2-one (4.32 g, 17.3 mmol), paraformaldehyde (0.99 g, 32.9 mmol), and morpholine (1.89 mL, 21.7 mmol) in 192 mL EtOH and 48 mL dioxane was heated at reflux for 18.5 h. The solution was concentrated in vacuo to a volume of 100 mL and then refluxed for 1 h to dissolve the precipitate. The mixture was allowed to cool to room temperature and the solid which formed was collected by filtration to give 4.19 g of a bright yellow solid. An additional 0.72 g of yellow solid was obtained by crystallization of the filtrate from ethyl acetate. The combined material was crystallized from ethyl acetate give the title compound (2.49 g, 41%) as a fine yellow needles.

$^1$H NMR (500 MHz, d$_6$-DMSO) δ9.67 (d, J=7.8 Hz, 1H), 7.91 (d, J=7.6Hz, 1H), 7.68 (m, 2H), 7.58 (m, 1H), 7.19 (m, 1H), 7.14 (d, J=7.3 Hz, 1H), 7.05 (m, 1H), 5.84 (s, 2H), 4.53 (s, 2H), 3,53 (m, 4H), 2.54 (br s, 4H).

EXAMPLE 17

Preparation of 5-Dimethylaminophthalide

Sodium cyanoborohydride (8.42 g, 134 mmol) was added into a stirred suspension of 5-aminophthalide (5.0 g, 33.5 mmol) and 37% CH$_2$O/H$_2$O solution (24.9 mL, 335 mmol) in 120 mL of acetonitrile. The mixture was stirred at room temperature for 1 hour, cooled to 0° C. and 120 mL of 10% aqueous acetic acid solution was added. The mixture was then stirred at room temperature for 1 hour, evaporated under low pressure until no acetonitrile remained. The resulting mixture was extracted with ethyl acetate (2×125 mL). The combined organic extracts were washed with saturated NaHCO$_3$ solution (125 mL) and brine (125 mL), dried over Na$_2$SO$_4$ and evaporated to dryness to give a light brown solid, which was triturated with hot MeOH (10 mL) to give the title compound (3.9 g, 66%) as an off-white solid.

EXAMPLE 18

Preparation of 3-(5-Dimethylamino-3H-isobenzofuran-1-ylidene)-1,3-dihydro-indol-2-one A solution of oxindole (938 mg, 7.05 mmol) in 20 mL of DME was cooled to 0° C., and treated with 6.2 mL of 2.5M n-BuLi/hexane solution (15.5 mmol) dropwise under nitrogen. The mixture was stirred at 0° C. for 10 minutes. 5-dimethylaninophthalide (1.0 g, 5.64 mmol) was added as one portion. The mixture was allowed to warm to room temperature under nitrogen and stirring was continued for 3 hours. The cloudy mixture was then slowly added into 0.5M aqueous HCl solution (0° C.) with vigorous stirring. The resulting mixture was neutralized with 1M NaOH solution until pH=9. The yellow precipitate which formed was collected by filtration, washed with water, dried under vacuum. The solid obtained was triturated with hot MeOH (20 mL), collected by filtration and dried to give title compound (990 mg, 60%) as a bright yellow powder.

EXAMPLE 19

Preparation of 3-(5-Dimethylamino-3H-isobenzofuran-1-ylidene)-1-piperidin-1-ylmethyl-1,3-dihydro-indol-2-one A mixture of 3-(5-Dimethylamino-3H-isobenzofuran-1-ylidene)-1,3-dihydro-indol-2-one (550 mg, 1.88 mmol), paraformaldehyde (141 mg, 4.7 mmol) and piperidine (240 mg, 2.82 mmol) in 20 mL of EtOH was stirred at reflux for overnight and cooled to room temperature. The solid which formed on cooling was collected by filtration, washed with EtOH (5 mL) and dried under vacuum to give the title compound (655 mg, 89%) as bright yellow crystals.

EXAMPLE 20

Preparation of 5-Chloro-3-(5-dimethylamino-3H-isobenzofuran-1-ylidene)-1,3-dihydro-indol-2-one A solution of 5-chlorooxindole (1.18 mg, 7.05 mmol) in 20 mL of DME was cooled to 0° C., and treated with 6.2 mL of 2.5M n-BuLi/hexane solution (15.5 mmol) dropwise under nitrogen. The mixture was stirred at 0° C. for 10 minutes. 5-dimethylaminophthalide (1.0 g, 5.64 mmol) was added as one portion. The mixture was allowed to warm to room temperature under nitrogen and stirring was continued for 3 hours. The cloudy mixture was then slowly added into 0.5M aqueous HCl solution (0° C.) with vigorous stirring. The resulting mixture was neutralized with 1M NaOH solution until pH=9. The yellow precipitate which formed was collected by filtration, washed with water, dried under vacuum. The solid obtained was triturated with hot MEOH (20 mL) followed by ethyl acetate (10 mL), collected by filtration and dried to give title compound (900 mg, 49%) as a bright yellow powder.

EXAMPLE 21

Preparation of 5-Chloro-3-(5-dimethylamino-3H-isobenzofuran-1-ylidene)-1-piperidin-1-ylmethyl-1,3-dihydro-indol-2-one A mixture of 5-Chloro-3-(5-dimethylamino-3H-isobenzofuran-1-ylidene)-1,3-dihydro-indol-2-one (400 mg, 1.22 mmol), paraformaldehyde (91 mg, 3.05 mmol) and piperidine (156 mg, 1.83 mmol) in 20 mL of EtOH was stirred at reflux for overnight and cooled to room temperature. The solid which formed on cooling was collected by filtration, washed with EtOH (5 mL) and dried under vacuum to give the title compound (500 mg, 97%) as bright yellow crystals.

The present invention is not to be limited in scope by the exemplified embodiments which are intended as illustrations of single aspects of the invention only. Indeed, various modifications of the invention in addition to those described herein will become apparent to those skilled in the art from the foregoing description. Such modifications are intended to fall within the scope of the appended claims.

All references cited herein are hereby incorporated by reference in their entirety.

What is claimed is:

1. A compound selected from the group consisting of

1-Piperidin-1-ylmethyl-3-(1-H-pyrrol-2-ylmethylene)-1,3-dihydro-indol-2-one,

1-Morpholin-4-ylmethyl-3-(1H-pyrrol-2-ylmethylene)-1,3-dihydro-indol-2-one, 1-(4-Methyl-piperazin-1-ylmethyl)-3-(1H-pyrrol-2-ylmethylene)-1,3-dihydro-indol-2-one, 1-[(3-Methoxy-propylamino)-methyl]-3-(1H-pyrrol-2-ylmethylene)-1,3-dihydro-indol-2-one, 1-Butylaminomethyl-3-(1H-pyrrol-2-ylmethylene)-1,3-dihydro-indol-2-one, 5-Chloro-3-(3,5-dimethyl-1H-pyrrol-2-ylmethylene)-1-piperidin-1-ylmethyl-1,3-dihydro-indol-2-one, 5-Chloro-3-(3,5-dimethyl-1H-pyrrol-2-ylmethylene)-1-piperidin-1-ylmethyl-1,3-dihydro-indol-2-one, 5-Chloro-3-(3,5-dimethyl-1H-pyrrol-2-ylmethylene)-1-morpholin-4-ylmethyl-1,3-dihydro-indol-2-one, 3-(3H-Isobenzofuran-1-ylidene)-1-piperidin-1-ylmethyl-1,3-dihydro-indol-2-one and 3-(3H-Isobenzofuran-1-ylidene)-1-morpholin-4-ylmethyl-1,3-dihydro-indol-2-one.

2. A method for treating diseases related to unregulated tyrosine kinase signal transduction, the method comprising the step of administering to a subject in need thereof a therapeutically effective amount of a compound according to claim 1.

3. The method of claim 2 wherein said disease is selected from the group consisting of cancer, blood vessel proliferative disorders, fibrotic disorders, mesangial cell proliferative disorders and metabolic diseases.

4. The method of claim 2 wherein the blood vessel proliferative disorder is selected from the group consisting of diabetic retinopathy, age-related macular degeneration, retinopathy of prematurity, arthritis and restenosis.

5. The method of claim 2 wherein the fibrotic disorder is selected from the group consisting of hepatic cirrhosis, atherosclerosis and surgical adhesions.

6. The method of claim 2 wherein the mesangial cell proliferative disorder is selected from the group consisting of glomerulonephritis, diabetic nephropathy, malignant nephrosclerosis, thrombotic microangiopathy syndromes, transplant rejection and glomerulopathies.

7. The method of claim 2 wherein the metabolic disorder is selected from the group consisting of psoriasis, diabetes mellitus, wound healing, inflammation and neurodegenerative diseases.

* * * * *